(12) United States Patent
Baril et al.

(10) Patent No.: US 11,051,795 B2
(45) Date of Patent: Jul. 6, 2021

(54) TISSUE RETRIEVAL BAG

(71) Applicant: COVIDIEN LP, Mansfield, MA (US)

(72) Inventors: Jacob C. Baril, Norwalk, CT (US);
Saumya Banerjee, Hamden, CT (US);
Scott J. Prior, Shelton, CT (US)

(73) Assignee: Covidien LP, Mansfield, MA (US)

( * ) Notice: Subject to any disclaimer, the term of this patent is extended or adjusted under 35 U.S.C. 154(b) by 41 days.

(21) Appl. No.: 16/527,099

(22) Filed: Jul. 31, 2019

(65) Prior Publication Data
US 2021/0030406 A1  Feb. 4, 2021

(51) Int. Cl.
*A61B 17/00*    (2006.01)
*A61B 34/35*    (2016.01)

(52) U.S. Cl.
CPC ........ *A61B 17/00234* (2013.01); *A61B 34/35* (2016.02); *A61B 2017/00287* (2013.01); *A61B 2017/00477* (2013.01); *A61B 2017/00867* (2013.01)

(58) Field of Classification Search
CPC . A61B 17/00234; A61B 17/22; A61B 17/221; A61B 34/35; A61B 2017/00477; A61B 2017/00867; A61B 2017/00287; A61B 2017/00292; A61B 2017/00296; B65D 35/32; B65D 35/02; B65D 35/28
See application file for complete search history.

(56) References Cited

U.S. PATENT DOCUMENTS

| | | | |
|---|---|---|---|
| 5,341,815 A * | 8/1994 | Cotone | A61B 17/00234 600/562 |
| 6,059,793 A | 5/2000 | Pagedas | |
| 6,156,055 A | 12/2000 | Ravenscroft | |
| 6,162,209 A | 12/2000 | Gobron et al. | |
| 6,171,317 B1 | 1/2001 | Jackson et al. | |
| 6,206,889 B1 | 3/2001 | Bennardo | |
| 6,224,612 B1 | 5/2001 | Bates et al. | |
| 6,228,095 B1 | 5/2001 | Dennis | |
| 6,248,113 B1 | 6/2001 | Fina | |
| 6,258,102 B1 | 7/2001 | Pagedas | |
| 6,264,663 B1 | 7/2001 | Cano | |
| 6,270,505 B1 | 8/2001 | Yoshida et al. | |
| 6,280,451 B1 | 8/2001 | Bates et al. | |
| 6,344,026 B1 | 2/2002 | Burbank et al. | |
| 6,350,266 B1 | 2/2002 | White et al. | |
| 6,350,267 B1 | 2/2002 | Stefanchik | |

(Continued)

*Primary Examiner* — Erich G Herbermann
(74) *Attorney, Agent, or Firm* — Carter, DeLuca & Farrell LLP

(57) ABSTRACT

A tissue retrieval bag includes a brim selectively transitionable between a first configuration in which a bag mouth is biased open and a second configuration in which the brim is compressed. A bag body extends from the brim and defines a pouch for holding a tissue specimen. The bag body includes at least one spine operably associated with the brim. The spine reversibly furls and unfurls the bag body. A first release tab is operably coupled to the brim to contain the brim in the second configuration. The first release tab, upon release thereof, transitions the brim from the second configuration to the first configuration. At least one second release tab is operably coupled to the brim to maintain the bag body furled about the brim. Upon release of the at least one second release tab, the at least one spine unfurls the bag body from the brim.

20 Claims, 4 Drawing Sheets

(56) References Cited

U.S. PATENT DOCUMENTS

| | | |
|---|---|---|
| 6,358,198 B1 | 3/2002 | Levin et al. |
| 6,368,328 B1 | 4/2002 | Chu et al. |
| 6,383,195 B1 | 5/2002 | Richard |
| 6,383,197 B1 | 5/2002 | Conlon et al. |
| 6,387,102 B2 | 5/2002 | Pagedas |
| 6,406,440 B1 | 6/2002 | Stefanchik |
| 6,409,733 B1 | 6/2002 | Conlon et al. |
| 6,447,523 B1 | 9/2002 | Middleman et al. |
| 6,530,923 B1 | 3/2003 | Dubrul et al. |
| 6,537,273 B1 | 3/2003 | Sosiak et al. |
| 6,752,822 B2 | 6/2004 | Jespersen |
| 6,805,699 B2 | 10/2004 | Shimm |
| 6,951,533 B2 | 10/2005 | Foley |
| 6,986,774 B2 | 1/2006 | Middleman et al. |
| 7,037,275 B1 | 5/2006 | Marshall et al. |
| 7,052,501 B2 | 5/2006 | McGuckin, Jr. |
| 7,087,062 B2 | 8/2006 | Dhindsa |
| 7,101,379 B2 | 9/2006 | Gregory, Jr. et al. |
| 7,101,380 B2 | 9/2006 | Khachin et al. |
| 7,112,172 B2 | 9/2006 | Orban, III et al. |
| 7,115,125 B2 | 10/2006 | Nakao et al. |
| 7,144,400 B2 | 12/2006 | Byrum et al. |
| 7,169,154 B1 | 1/2007 | Que et al. |
| 7,229,418 B2 | 6/2007 | Burbank et al. |
| 7,285,126 B2 | 10/2007 | Sepetka et al. |
| 7,316,692 B2 | 1/2008 | Huffmaster |
| 7,357,801 B2 | 4/2008 | Burbank et al. |
| 7,534,252 B2 | 5/2009 | Sepetka et al. |
| 7,547,310 B2 | 6/2009 | Whitfield |
| 7,615,013 B2 | 11/2009 | Clifford et al. |
| 7,618,437 B2 | 11/2009 | Nakao |
| 7,654,283 B2 | 2/2010 | Seto et al. |
| 7,670,346 B2 | 3/2010 | Whitfield |
| 7,678,118 B2 | 3/2010 | Bates et al. |
| 7,722,626 B2 | 5/2010 | Middleman et al. |
| 7,727,227 B2 | 6/2010 | Teague et al. |
| 7,731,722 B2 | 6/2010 | Lavelle et al. |
| 7,731,723 B2 | 6/2010 | Kear et al. |
| 7,762,959 B2 | 7/2010 | Bilsbury |
| 7,762,960 B2 | 7/2010 | Timberlake et al. |
| 7,875,038 B2 | 1/2011 | Que et al. |
| 7,892,242 B2 | 2/2011 | Goldstein |
| 7,914,540 B2 | 3/2011 | Schwartz et al. |
| 7,918,860 B2 | 4/2011 | Leslie et al. |
| 7,955,292 B2 | 6/2011 | Leroy et al. |
| 8,057,485 B2 | 11/2011 | Hollis et al. |
| 8,075,567 B2 | 12/2011 | Taylor et al. |
| 8,118,816 B2 | 2/2012 | Teague |
| 8,152,820 B2 | 4/2012 | Mohamed et al. |
| 8,172,772 B2 | 5/2012 | Zwolinski et al. |
| 8,211,115 B2 | 7/2012 | Cheng et al. |
| 8,282,572 B2 | 10/2012 | Bilsbury |
| 8,337,510 B2 | 12/2012 | Rieber et al. |
| 8,348,827 B2 | 1/2013 | Zwolinski |
| 8,409,216 B2 | 4/2013 | Parihar et al. |
| 8,414,596 B2 | 4/2013 | Parihar et al. |
| 8,419,749 B2 | 4/2013 | Shelton, IV et al. |
| 8,425,533 B2 | 4/2013 | Parihar et al. |
| 8,430,826 B2 | 4/2013 | Uznanski et al. |
| 8,435,237 B2 | 5/2013 | Bahney |
| 8,444,655 B2 | 5/2013 | Parihar et al. |
| 8,486,087 B2 | 7/2013 | Fleming |
| 8,512,351 B2 | 8/2013 | Teague |
| 8,579,914 B2 | 11/2013 | Menn et al. |
| 8,585,712 B2 | 11/2013 | O'Prey et al. |
| 8,591,521 B2 | 11/2013 | Cherry et al. |
| 8,652,147 B2 | 2/2014 | Hart |
| 8,721,658 B2 | 5/2014 | Kahle et al. |
| 8,734,464 B2 | 5/2014 | Grover et al. |
| 8,777,961 B2 | 7/2014 | Cabrera et al. |
| 8,795,291 B2 | 8/2014 | Davis et al. |
| 8,821,377 B2 | 9/2014 | Collins |
| 8,827,968 B2 | 9/2014 | Taylor et al. |
| 8,870,894 B2 | 10/2014 | Taylor et al. |
| 8,906,035 B2 | 12/2014 | Zwolinski et al. |
| 8,956,370 B2 | 2/2015 | Taylor et al. |
| 8,968,329 B2 | 3/2015 | Cabrera |
| 8,986,321 B2 | 3/2015 | Parihar et al. |
| 9,005,215 B2 | 4/2015 | Grover et al. |
| 9,017,328 B2 | 4/2015 | Bahney |
| 9,017,340 B2 | 4/2015 | Davis |
| 9,033,995 B2 | 5/2015 | Taylor et al. |
| 9,084,588 B2 | 7/2015 | Farascioni |
| 9,101,342 B2 | 8/2015 | Saleh |
| 9,113,848 B2 | 8/2015 | Fleming et al. |
| 9,113,849 B2 | 8/2015 | Davis |
| 9,308,008 B2 | 4/2016 | Duncan et al. |
| 9,364,201 B2 | 6/2016 | Orban, III |
| 9,364,202 B2 | 6/2016 | Menn et al. |
| 9,370,341 B2 | 6/2016 | Ceniccola et al. |
| 9,370,378 B2 | 6/2016 | O'Prey et al. |
| 9,375,224 B2 | 6/2016 | Jansen |
| 9,414,817 B2 | 8/2016 | Taylor et al. |
| 9,468,542 B2 | 10/2016 | Hurley et al. |
| 9,486,188 B2 | 11/2016 | Secrest et al. |
| 9,522,034 B2 | 12/2016 | Johnson et al. |
| 9,549,747 B2 | 1/2017 | Carlson |
| 9,579,115 B2 | 2/2017 | Kahle et al. |
| 9,592,067 B2 | 3/2017 | Hartoumbekis |
| 9,622,730 B2 | 4/2017 | Farascioni |
| 9,624,638 B2 | 4/2017 | Lebreton et al. |
| 9,629,618 B2 | 4/2017 | Davis et al. |
| 9,655,644 B2 | 5/2017 | Collins |
| 9,730,716 B2 | 8/2017 | Secrest et al. |
| 9,789,268 B2 | 10/2017 | Hart et al. |
| 9,808,228 B2 | 11/2017 | Kondrup et al. |
| 9,826,997 B2 | 11/2017 | Cherry et al. |
| 9,867,600 B2 | 1/2018 | Parihar et al. |
| 9,877,893 B2 | 1/2018 | Taylor et al. |
| 2005/0165412 A1* | 7/2005 | Secrest ............ A61B 17/00234 606/127 |

* cited by examiner

TISSUE RETRIEVAL BAG

BACKGROUND

Technical Field

The present disclosure relates to tissue retrieval devices and, more particularly, to a compressible tissue retrieval bag to facilitate retrieval of a tissue specimen from an internal body cavity.

Background of Related Art

In minimally-invasive surgical procedures, operations are carried out within an internal body cavity through small entrance openings in the body. The entrance openings may be natural passageways of the body or may be surgically created, for example, by making a small incision into which a cannula is inserted.

Minimally-invasive surgical procedures may be used for partial or total retrieval of a tissue specimen from an internal body cavity. However, the restricted access provided by minimally-invasive openings (natural passageways and/or surgically created openings) presents challenges with respect to maneuverability and visualization. The restricted access also presents challenges when the tissue specimen is required to be removed. As such, a tissue specimen that is deemed too large for intact retrieval may be broken down into a plurality of smaller pieces to facilitate retrieval from the internal body cavity.

During such minimally-invasive surgical procedures, it is common that a cyst, tumor, or other affected tissue specimen is required to be removed. In these and other procedures where cancerous tissue is required to be removed, retrieval of the tissue specimen in an enclosed environment is desirable to inhibit seeding of cancer cells. Thus, with respect to breaking down large tissue specimens for retrieval through minimally-invasive openings, there is the added challenge of doing so within an enclosed environment.

A tissue retrieval bag is an option for removing and breaking town a tissue specimen.

SUMMARY

In accordance with an aspect of the present disclosure, a tissue retrieval bag includes a brim defining a bag mouth. The brim is selectively transitionable between a first configuration in which the bag mouth is biased open and a second configuration in which the brim is compressed. A bag body extends from the brim and defines a pouch for holding a tissue specimen. The bag body includes at least one spine operably associated with the brim and depending therefrom. The spine reversibly furls and unfurls the bag body about the brim. A first release tab is operably coupled to the brim to contain the brim in the second configuration. The first release tab, upon release thereof, transitions the brim from the second configuration to the first configuration. At least one second release tab is operably coupled to the brim to maintain the bag body furled about the brim. Upon release of the at least one second release tab, the at least one spine unfurls the bag body from the brim.

In some aspects, the brim includes a shape memory alloy made from at least one of nickel or titanium.

In some aspects, the at least one spine includes a shape memory alloy made from at least one of nickel or titanium.

In some aspects, the brim in the first configuration includes a substantially elliptical shape. The brim has a diameter of less than about 15 mm.

In some aspects, the first release tab includes a perforated edge defined between a first side and a second side of the brim. The first release tab includes a release tether configured to separate the first release tab along the perforated edge upon actuation thereof. The release tether includes an external pull configured for positioning outside of a patient's body cavity.

In some aspects, the at least one second release tab includes a first release flap coupled to a first side of the brim and a second release flap coupled to a second side of the brim. The first and second release flaps each include a perforated edge defined therein. The first and second release flaps are connected to each other by a tether. The tether substantially simultaneously separates the first and second release flaps along the perforated edges of the first and second release flaps upon actuation thereof. The tether includes an external pull configured for positioning outside of a patient's body cavity.

In accordance with an aspect of the present disclosure, a tissue retrieval bag includes a brim defining a bag mouth. The brim is selectively transitionable between a first configuration in which the bag mouth is biased open and a second configuration in which the brim is compressed. The second configuration is sufficiently narrow to allow passage of the tissue retrieval bag through a shaft of a surgical instrument. A bag body extends from the brim. The bag body includes at least one spine operably associated with the brim and depending therefrom. The spine reversibly furls and unfurls the bag body about the brim. The bag body is sufficiently narrow when furled to allow passage of the tissue retrieval bag through a shaft of a surgical instrument. A first release tab is operably coupled to the brim to contain the brim in the second configuration. The first release tab, upon release thereof, transitions the brim from the second configuration to the first configuration. At least one second release tab is operably coupled to the brim to maintain the bag body furled about the brim. Upon release of the at least one second release tab, the at least one spine unfurls the bag body from the brim.

BRIEF DESCRIPTION OF THE DRAWINGS

The accompanying drawings, which are incorporated in and constitute a part of this specification, illustrate embodiments of the present disclosure and, together with the detailed description below, serve to further explain the present disclosure, in which.

DETAILED DESCRIPTION

Figure 1A:
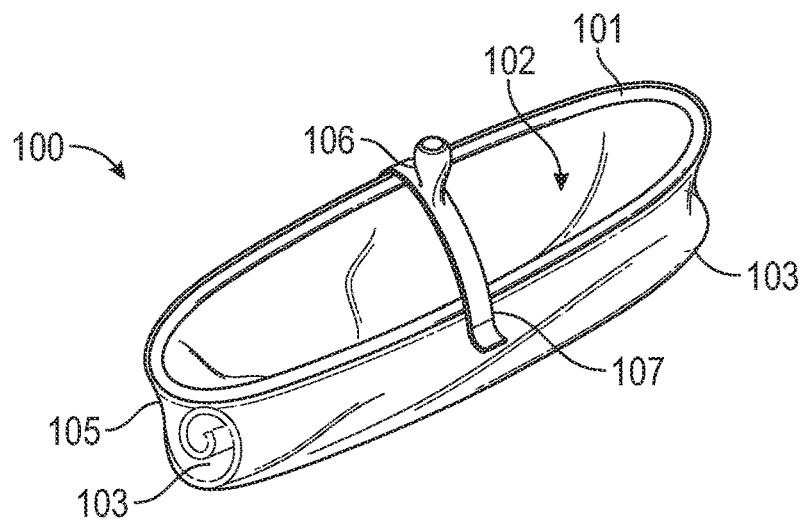
FIG. 1A is a side, perspective view of a tissue retrieval bag having a brim in a compressed state in accordance with the present disclosure.

As used herein, the term "distal" refers to the portion that is being described which is further from a user, while the term "proximal" refers to the portion that is being described which is closer to a user. Further, to the extent consistent, any of the aspects and features detailed herein may be used in conjunction with any or all of the other aspects and features detailed herein.

As used herein, the terms parallel and perpendicular are understood to include relative configurations that are substantially parallel and substantially perpendicular up to about + or −10 degrees from true parallel and true perpendicular.

"About" or "approximately" as used herein may be inclusive of the stated value and means within an acceptable range of variation for the particular value as determined by one of ordinary skill in the art, considering the measurement in question and the error associated with measurement of the particular quantity (e.g., the limitations of the measurement system). For example, "about" may mean within one or more standard variations, or within ±30%, 20%, 10%, 5% of the stated value.

Descriptions of technical features or aspects of an exemplary embodiment of the present disclosure should typically be considered as available and applicable to other similar features or aspects in another exemplary embodiment of the present disclosure. Accordingly, technical features described herein according to one exemplary embodiment of the present disclosure may be applicable to other exemplary embodiments of the present disclosure, and thus duplicative descriptions may be omitted herein.

Exemplary embodiments of the present disclosure will be described more fully below (e.g., with reference to the accompanying drawings). Like reference numerals may refer to like elements throughout the specification and drawings.

Referring to FIGS. 1A, 1B, 1C, 2A, 2B and 2C, in accordance with an aspect of the present disclosure, a tissue retrieval bag 100 includes a brim 101 defining a bag mouth 102. The brim 101 is selectively transitionable between a first configuration (see, e.g., FIG. 1B) in which the bag mouth 102 is biased open and a second configuration (see, e.g., FIG. 1A) in which the brim 101 is compressed (e.g., to cinch the bag mouth 102 closed). A bag body 103 extends from the brim 101 and defines a pouch 104 for holding a tissue specimen. The bag body 103 including at least one spine 105 is operably associated with the brim 101 and depends therefrom. The spine 105 is configured to enable the bag body 103 to furl and unfurl about the brim 101. For example, the spine 105 may be in a rolled up configuration (see, e.g., FIG. 1B) before the release of a second release tab (e.g., second release tab 107) which allows the spine 105 to return to an initial shape/configuration to unfurl the bag body 103 as described in more detail below. In some aspects, two spines 105 may be respectively positioned on two sides of the brim 101, such as at opposite sides of the brim 101. Thus, opposite sides of the bag body 103 may be substantially simultaneously unfurled by the two spines 105 upon release of the second release tab 107.

Various release tabs and/or releases are described in more detail below and allow the tissue retrieval bag 100 to be compressed for insertion through a shaft of a surgical instrument (e.g., having a 15 mm port), incision or natural body orifice. The tissue retrieval bag 100 may be selectively compressible or provided in a pre-compressed state depending upon a particular purpose. For the purposes herein, the tissue specimen bag 100 is described in a pre-state to facilitate introduction into a surgical cavity. For example, when the tissue retrieval bag 100 has the brim 101 compressed in the second configuration and the bag body 103 in the furled state, the tissue retrieval bag 100 is sufficiently sized (e.g., is sufficiently narrow) to allow passage of the tissue retrieval bag 100 through a shaft of a surgical instrument, or through an incision or natural body orifice.

Figure 1B:
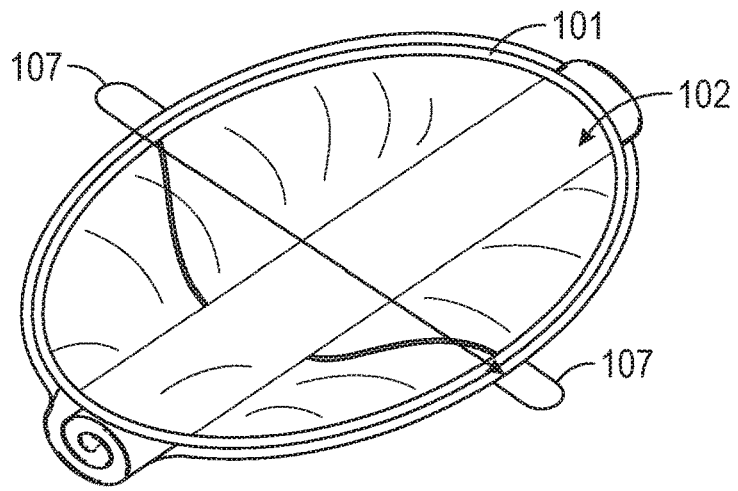
FIG. 1B is a top, perspective view of the tissue retrieval bag of FIG. 1A in an open state after release of a first release tab.
Figure 1C:
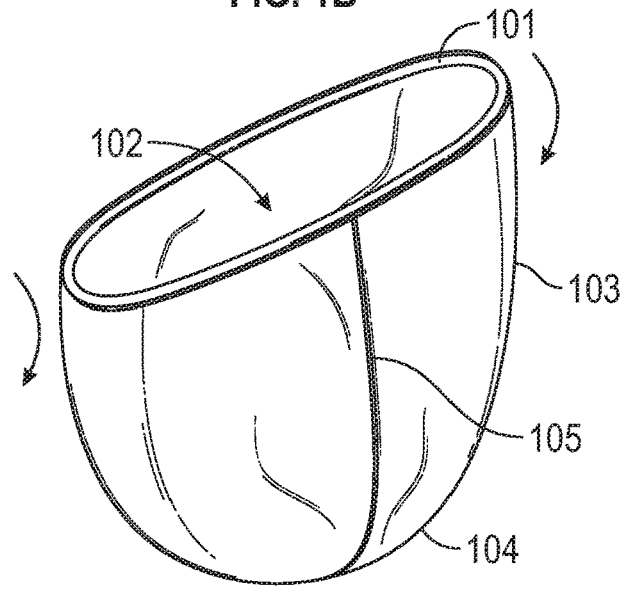
FIG. 1C is a side, perspective view of the tissue retrieval bag of FIG. 1A in an unfurled state after release of a second release tab.
Figure 2A:
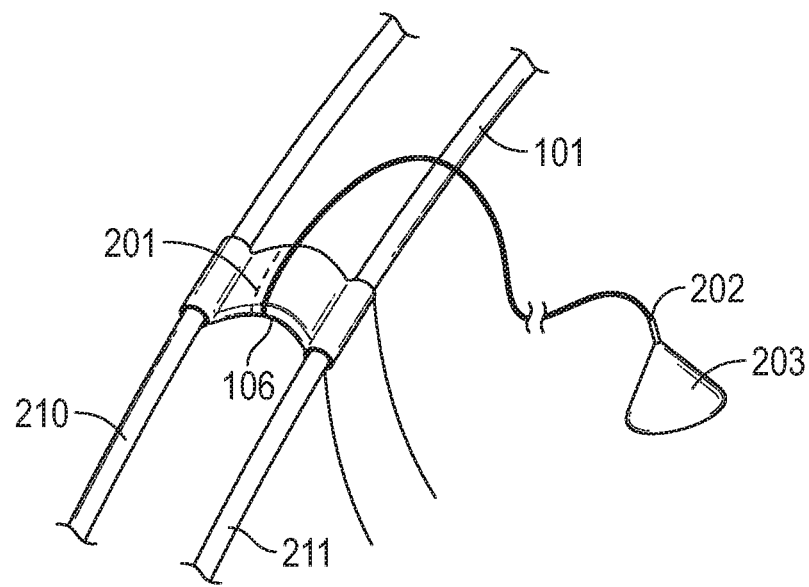
FIG. 2A is an enlarged top, perspective view of a brim of the tissue retrieval bag of FIG. 1A in the compressed state with the first release tab operably coupled to the brim in accordance with the present disclosure.
Figure 2B:
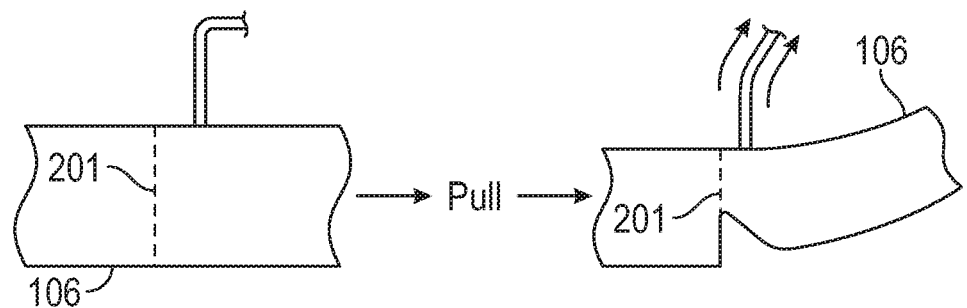
FIG. 2B is an enlarged, top view of the first release tab operably coupled to the brim and having a perforated edge in accordance with the present disclosure.
Figure 2C:
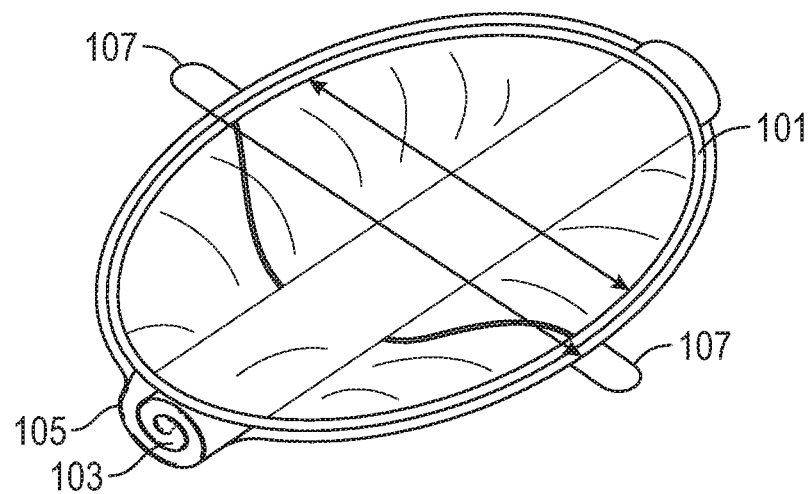
FIG. 2C is a top, perspective view of the tissue retrieval bag of FIG. 1A in the open state with the second release tab operably coupled to the brim in accordance with the present disclosure.
Figure 3A:
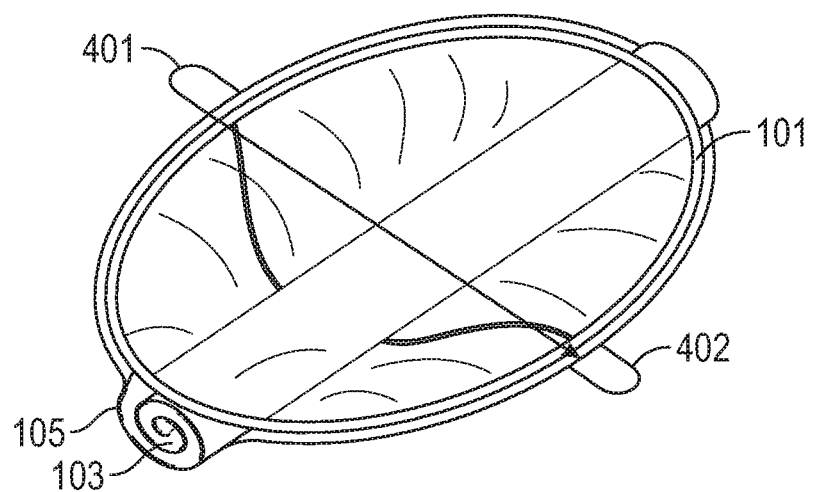
FIG. 3A is a top, perspective view of the tissue retrieval bag in the open state with the bag furled and two second release tabs operably coupled to the brim in accordance with the present disclosure.
Figure 3B:
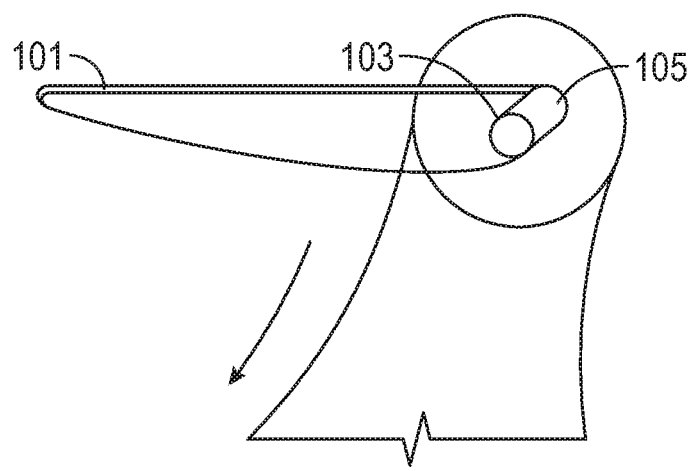
FIG. 3B is a side view of the tissue retrieval bag of FIG. 3A in the open state and the bag furled before release of the second release tabs.
Figure 3C:
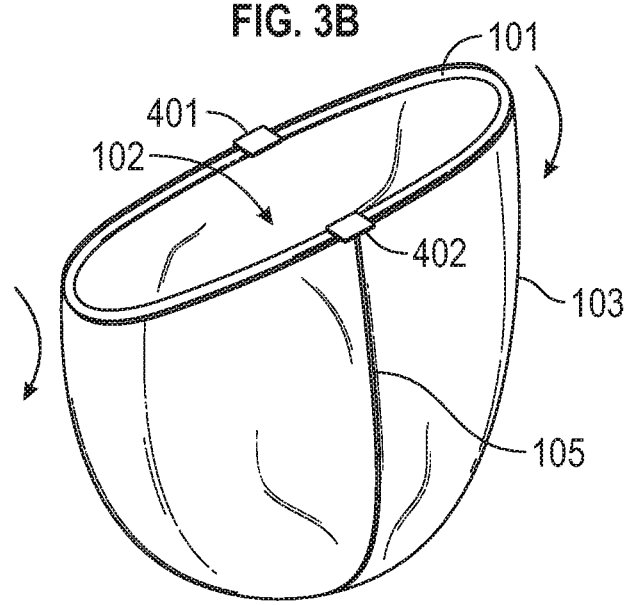
FIG. 3C is a side, perspective view of the tissue retrieval bag of FIG. 3A in the open state and the bag unfurled after release of the two second release tabs in accordance with the present disclosure.
Figure 4A:
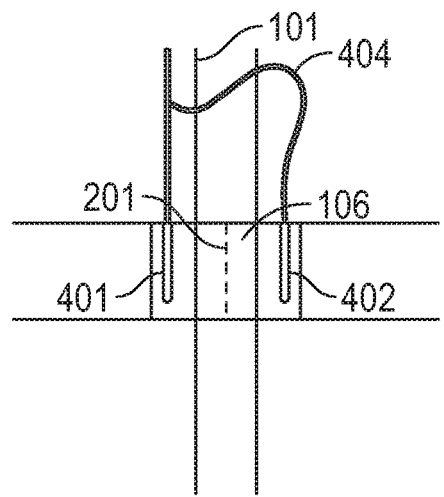
FIG. 4A is an enlarged, top view of the of the brim of the tissue retrieval bag of FIG. 3A in the compressed state with the first release tab operably coupled to the brim and two second release tabs each having perforated edges operably coupled to the brim in accordance with the present disclosure.
Figure 4B:
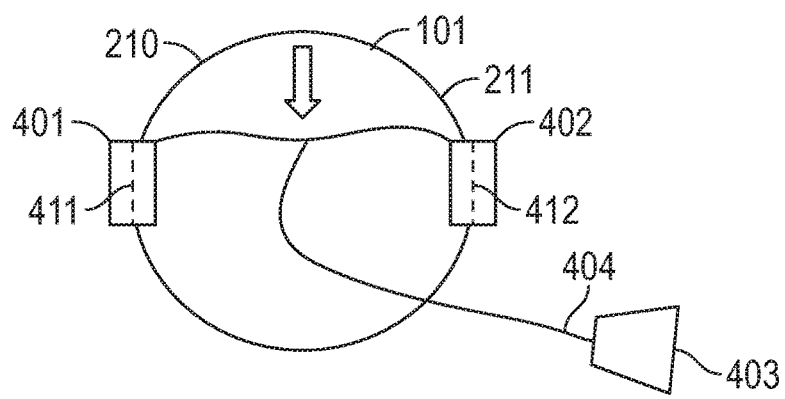
FIG. 4B is an enlarged, top view of the tissue retrieval bag of FIG. 4A in the open state and the bag furled before release of the second release tabs.
Figure 4C:
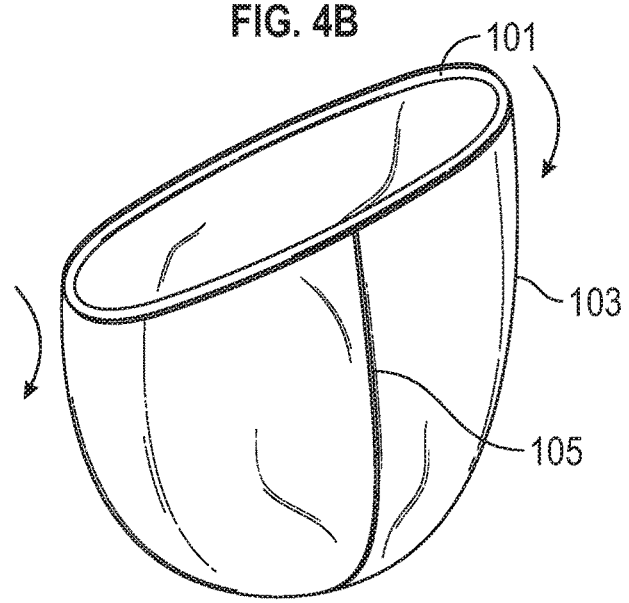
FIG. 4C is a side, perspective view of the tissue retrieval bag of FIG. 4A in the open state and the bag unfurled after release of the two second release tabs.

Turing back to FIGS. 1A-1C, a first release tab 106 is operably coupled to the brim 101. The first release tab 106 holds the brim 101 in the second configuration (i.e., a compressed state) The first release tab 106, upon release thereof, causes the bias of the brim 101 to transition the bag brim 101 from the second configuration (i.e., a compressed configuration) to the first configuration (i.e., an uncompressed or open state).

As mentioned above, one or more second release tabs 107 is operably coupled to the brim 101. Second release tab(s) 107, upon release thereof, allows one or more spines 105 to unfurl the bag body 103 about the brim 101 to deploy the bag body 103. While a single first release tab 107 may be operably coupled to the brim 101, two or more second release tabs 107 (see, e.g., FIG. 1B) may be operably coupled to the brim 101. Each of the second release tabs 107 may release a corresponding spine 105 to unfurl the bag body 103.

In some aspects, the brim 101 includes or is formed of a shape memory alloy including nickel and titanium. In some aspects, the spine 105 includes or is formed of a shape memory alloy including nickel and titanium. The brim 101 in the first configuration may be substantially elliptical and may have a width across one of its major or minor axes of less than about 15 mm.

The first release tab 106 includes a perforated edge 201 between a first side 210 and a second side 211 of the brim 101. The first release tab 106 is connected with a release tether 202 configured to separate the first release tab 106 along the perforated edge 201. Pulling the release tether 202 separates the first release tab 106 along the perforated edge 201 to transition the brim 101 to the first open configuration. The release tether 202 may include an external pull 203 configured for positioning outside a patient's body cavity or therewithin.

The tissue retrieval bag described below with reference to FIGS. 3A, 3B, 3C, 4A, 4B and 4C is substantially the same as the tissue retrieval bag 100 described above with reference to FIGS. 1A-2C unless otherwise indication. Thus duplicative descriptions may be omitted below.

Referring to FIGS. 3A, 3B, 3C, 4A, 4B and 4C, in one embodiment, second release tab(s) 107 includes a first release flap 401 coupled to a first side 210 of the brim and a second release flap 402 coupled to a second side 211 of the brim 101. The first and second release flaps 401 and 402 of second release tab 107 each include a perforated edge 411 and 412, respectively, defined therealong. The first and second release flaps 401 and 402 of the second release tab 107 are connected to each other by a tether 404. The tether 404 substantially simultaneously separates the first and second release flaps 401 and 402 of the second release tab 107 along the respective perforated edges 411 and 412 of the first and second release flaps 401 and 402 (e.g., after the first release tab 106 has been separated—see, e.g., FIGS. 4A-4C). The tether 404 includes an external pull 403 configured for positioning outside of a patient's body cavity or therewithin.

A further description of a tissue retrieval bag according to the present disclosure can be found in U.S. patent application Ser. No. 16/391,408, filed on Apr. 23, 2019, the disclosure of which is incorporated by reference herein in its entirety.

The various embodiments disclosed herein may also be configured to work with robotic surgical systems and what is commonly referred to as "Telesurgery." Such systems employ various robotic elements to assist the surgeon and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prep the patient for surgery and configure the robotic surgical system with one or more of the instruments disclosed herein while another surgeon (or group of surgeons) remotely control the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A tissue retrieval bag, comprising:
    a brim defining a bag mouth, the brim selectively transitionable between a first configuration wherein the bag mouth is biased open and a second configuration wherein the brim is compressed;
    a bag body extending from the brim and defining a pouch configured to contain a tissue specimen therein, the bag body including at least one spine operably associated with the brim and depending therefrom, the at least one spine configured to reversibly furl and unfurl the bag body about the brim;
    a first release tab operably coupled to the brim, the first release tab configured to contain the brim in the second configuration such that, upon release thereof, the brim transitions from the second configuration to the first configuration, wherein the first release tab includes a perforated edge defined between a first side and a second side of the brim; and
    at least one second release tab operably coupled to the brim, the at least one second release tab configured to maintain the bag body furled about the brim such that, upon release thereof, the at least one spine unfurls the bag body from the brim.

2. The tissue retrieval bag of claim 1, wherein the brim includes a shape memory alloy made from at least one of nickel or titanium.

3. The tissue retrieval bag of claim 1, wherein the at least one spine includes a shape memory alloy made from at least one of nickel or titanium.

4. The tissue retrieval bag of claim 1, wherein the brim in the first configuration includes a substantially elliptical shape.

5. The tissue retrieval bag of claim 4, wherein the brim in the first configuration has a diameter along a minor axis of less than about 15 mm.

6. The tissue retrieval bag of claim 1, wherein the first release tab includes a release tether configured to separate the first release tab along the perforated edge upon actuation thereof.

7. The tissue retrieval bag of claim 6, wherein the release tether includes an external pull configured for positioning outside of a patient's body cavity.

8. The tissue retrieval bag of claim 1, wherein the at least one second release tab includes a first release flap coupled to the first side of the brim and a second release flap coupled to the second side of the brim.

9. The tissue retrieval bag of claim 8, wherein the first and second release flaps each include a perforated edge defined therein.

10. The tissue retrieval bag of claim 9, wherein the first and second release flaps are connected to each other by a tether.

11. The tissue retrieval bag of claim 10, wherein the tether is configured to substantially simultaneously separate the first and second release flaps along the perforated edges of the first and second release flaps upon actuation thereof.

12. The tissue retrieval bag of claim 10, wherein the tether includes an external pull configured for positioning outside of a patient's body cavity.

13. A tissue retrieval bag, comprising: a brim defining a bag mouth, the brim selectively transitionable between a first configuration wherein the bag mouth is biased open and a second configuration wherein the brim is compressed, the second configuration being sufficiently narrow to allow passage of the tissue retrieval bag through a shaft of a surgical instrument; a bag body extending from the brim, the bag body including at least one spine operably associated with the brim and depending therefrom, the at least one spine configured to reversibly furl and unfurl the bag body about the brim, the bag body being sufficiently narrow when furled to allow passage of the tissue retrieval bag through the shaft of the surgical instrument; a first release tab operably coupled to the brim, the first release tab configured to contain the brim in the second configuration such that, upon release thereof, the brim transitions from the second configuration to the first configuration, wherein the first release tab includes a perforated edge defined between a first side and a second side of the brim; and at least one second release tab operably coupled to the brim, the at least one second release tab configured to maintain the bag body furled about the brim such that, upon release thereof, the at least one spine unfurls the bag body from the brim.

14. The tissue retrieval bag of claim 13, wherein the brim includes a shape memory alloy made from at least one of nickel or titanium.

15. The tissue retrieval bag of claim 13, wherein the at least one spine includes a shape memory alloy made from at least one of nickel or titanium.

16. The tissue retrieval bag of claim 13, wherein the first release tab includes a release tether configured to separate the first release tab along the perforated edge upon actuation thereof.

17. The tissue retrieval bag of claim 13, wherein the at least one second release tab comprises a first release flap coupled to the first side of the brim and a second release flap coupled to the second side of the brim.

18. The tissue retrieval bag of claim 17, wherein the first and second release flaps are connected to each other by a tether.

19. A tissue retrieval bag, comprising:
a brim defining a bag mouth, the brim selectively transitionable between a first configuration wherein the bag mouth is biased open and a second configuration wherein the brim is compressed;
a bag body extending from the brim and defining a pouch configured to contain a tissue specimen therein, the bag body including at least one spine operably associated with the brim and depending therefrom, the spine configured to reversibly furl and unfurl the bag body about the brim;
a first release tab operably coupled to the brim, the first release tab configured to contain the brim in the second configuration such that, upon release thereof, the brim transitions from the second configuration to the first configuration; and
at least one second release tab operably coupled to the brim, the at least one second release tab configured to maintain the bag body furled about the brim such that, upon release thereof, the at least one spine unfurls the bag body from the brim, wherein the at least one second release tab includes a first release flap coupled to a first side of the brim and a second release flap coupled to a second side of the brim.

20. A tissue retrieval bag, comprising: a brim defining a bag mouth, the brim selectively transitionable between a first configuration wherein the bag mouth is biased open and a second configuration wherein the brim is compressed, the second configuration being sufficiently narrow to avow passage of the tissue retrieval bag through a shaft of a surgical instrument; a bag body extending from the brim, the bag body including at least one spine operably associated with the brim and depending therefrom, the spine configured to reversibly furl and unfurl the bag body about the brim, the bag body being sufficiently narrow when furled to avow passage of the tissue retrieval bag through the shaft of the surgical instrument; a first release tab operably coupled to the brim, the first release tab configured to contain the brim in the second configuration such that, upon release thereof, the brim transitions from the second configuration to the first configuration; and at least one second release tab operably coupled to the brim, the at least one second release tab configured to maintain the bag body furled about the brim such that, upon release thereof, the at least one spine unfurls the bag body from the brim, wherein the at least one second release tab comprises a first release flap coupled to a first side of the bag mouth and a second release flap coupled to a second side of the bag mouth.

* * * * *